United States Patent [19]

Girard et al.

[11] 4,228,242
[45] Oct. 14, 1980

[54] ARRANGEMENT FOR CULTIVATING CELLS OF ANIMAL AND HUMAN TISSUES

[75] Inventors: Henry Girard, Burtigny; Rudolf Bühler, Wolfhausen, both of Switzerland

[73] Assignee: Chemap AG, Maennedorf, Switzerland

[21] Appl. No.: 934,315

[22] Filed: Aug. 16, 1978

[30] Foreign Application Priority Data

Aug. 16, 1977 [CH] Switzerland ............... 10058/77

[51] Int. Cl.³ ................................................. C12M 3/00
[52] U.S. Cl. ................................... 435/284; 435/310; 435/313
[58] Field of Search ................ 195/127, 142, 143; 435/284, 313, 310

[56] References Cited

U.S. PATENT DOCUMENTS

| 3,732,149 | 5/1973 | Santerno | 195/127 X |
| 3,812,016 | 5/1974 | Muller | 195/143 X |
| 3,827,943 | 8/1974 | Mann | 195/127 |
| 3,853,712 | 12/1974 | House et al. | 195/127 |
| 3,925,165 | 12/1975 | Muller | 195/142 X |
| 4,144,136 | 3/1979 | Corbeil | 195/142 |

Primary Examiner—R. B. Penland
Attorney, Agent, or Firm—Michael J. Striker

[57] ABSTRACT

An arrangement for cultivating cells of animal and human tissues in a monocellular layer and the like, has a container bounding an inner chamber for accommodating a nutrient medium, and a plurality of tubular supporting elements for supporting the cells and rotatable about an axis. The tubular rotatable elements extend in an axial direction of the inner chamber of the container. Additional elements are provided for rotating the tubular supporting elements. These additional rotating elements include an axle which defines the axis of rotation, and two end discs each arranged adjacent to and supporting one of the axial ends of the tubular supporting elements. The tubular supporting elements extend in a horizontal direction. However, they can be inclined at an angle relative to the horizontal direction by means of rotation of the end discs in mutually opposite directions.

11 Claims, 6 Drawing Figures

ARRANGEMENT FOR CULTIVATING CELLS OF ANIMAL AND HUMAN TISSUES

BACKGROUND OF THE INVENTION

The present invention relates to an arrangement for cultivating cells of animal and human tissues in a monocellular layer, and for augmenting viruses on these tissues.

Arrangements for the above-mentioned applications have been proposed in the art. A known arrangement has a supporting unit for supporting the cells which is located and rotates in a container for accommodating a nutrient medium. Such an arrangement is disclosed in the German Pat. No. 2,341,180. In this arrangement the container is located horizontally, and the supporting unit includes a horizontal shaft which carries curved plates. Such a construction has some disadvantages. The cells grow only on concave surfaces of the curved plates. As for convex surfaces of the curved plates, when the convex surfaces are moistened by the nutrient medium the cells slip from these surfaces whereby the fixation of the cells on the supporting elements becomes impossible. Another disadvantage of the known arrangement is a great consumption of the nutrient medium per plate surface unit. In order to moisten the entire surface of the supporting unit with the nutrient medium an excessive quantity of a frequently very expensive nutrient medium is required.

SUMMARY OF THE INVENTION

Accordingly, it is an object of the present invention to provide an arrangement for cultivating cells of animal and human tissues in a monocellular layer and the like, which avoids the disadvantages of the prior art.

More particularly, it is an object of the present invention to provide an arrangement for the above-mentioned applications, which occupies the least possible space and at the same time has a large surface for growing cells.

Another object of the present invention is to provide an arrangement for the above mentioned applications, in which a minimum quantity of the nutrient medium is utilized and at the same time an optimum quantity of cells is produced.

In keeping with these objects, and with others which will become apparent hereinafter, one feature of the present invention resides, briefly stated, in an arrangement which has a container bounding an inner chamber for accommodating a nutrient medium, means in said chamber for supporting the cells and rotatable about an axis which means includes a plurality of tubular supporting elements extending in an axial direction of the chamber, and means for rotating the tubular supporting elements about this axis.

When the arrangement is constructed in accordance with the present invention, it occupies the least possible space and has a large surface for growing cells. A minimum quantity of a nutrient medium is required, and at the same time an optimum quantity of cells is produced.

Another object of the present invention is that the rotating means may include an axle defining the axis of rotation of the tubular supporting elements, and at least two discs mounted on this axle and supporting the tubular supporting elements for rotation about this axis.

Still another feature of the present invention is that the above-mentioned discs may be located adjacent to and support axially spaced ends of the tubular supporting elements. At the same time, an additional disc may be provided to support the tubular supporting elements in the central region thereof.

A further feature of the present invention is that the arrangement may have means for fixing the tubular supporting elements to the discs. The fixing means may include a plurality of O-rings each fixing one of the tubular supporting elements to one of the discs.

Still a further feature of the present invention is that each of the tubular supporting elements has two end portions each of which extends radially inwardly toward an axis of the tubular supporting element and bounds an end opening of the tubular supporting element.

An additional feature of the present invention is that the arrangement has a plurality of additional supporting elements each formed by plates which are arranged in star-like manner and located in an inner passage of a respective one of the tubular supporting elements.

Still an additional feature of the present invention is that the tubular supporting elements may be constituted by glass, whereas the additional star-like supporting elements may be constituted by polycarbonate.

Finally, a concomitant feature of the present invention is that the tubular supporting elements may be inclined relative to a horizontal position, preferably by means of displacement of the two supporting end discs in two opposite directions.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF A PREFERRED EMBODIMENT

Figure 1:
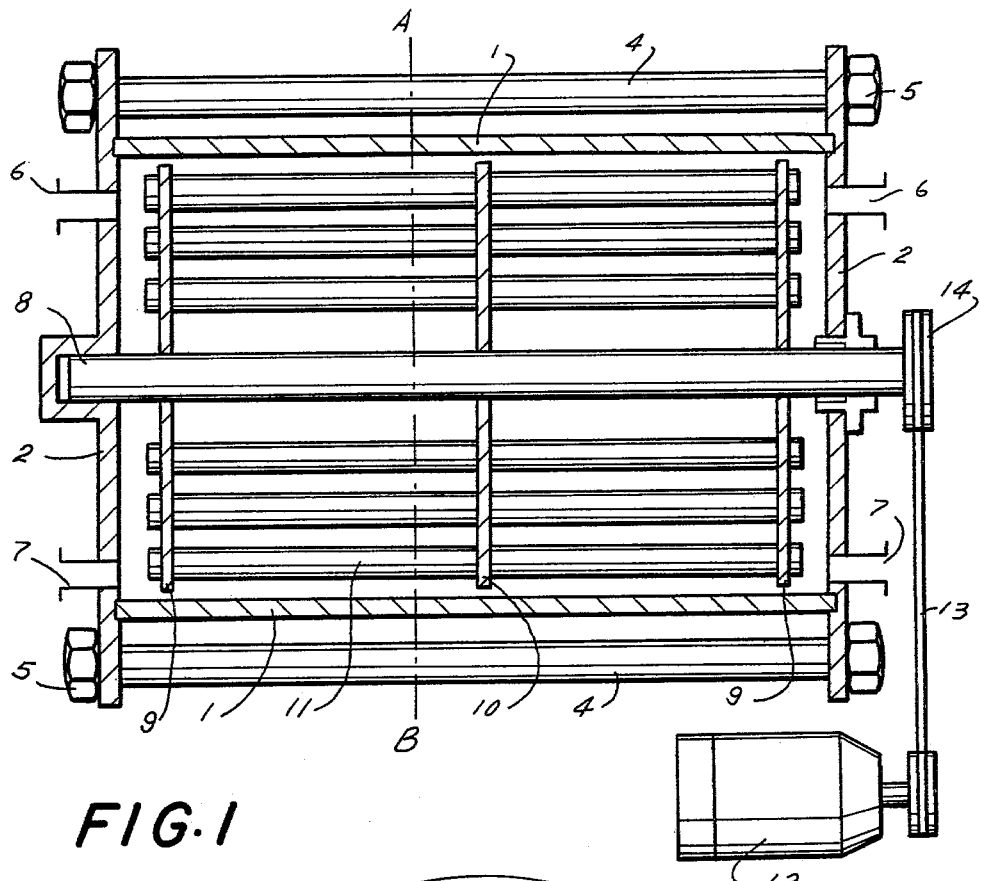
FIG. 1 is a view showing a longitudinal section of an arrangement for cultivating cells and the like in accordance with the present invention.
Figure 2:
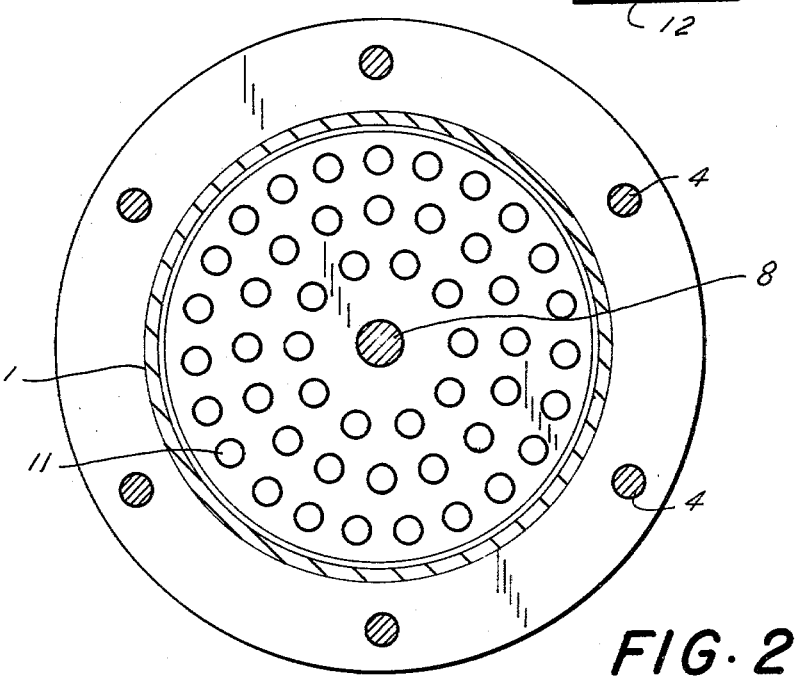
FIG. 2 is a view showing a section of the arrangement, taken along the line A–B in FIG. 1.

An arrangement for cultivating cells of animal and human tissues and for augmenting viruses on the tissues are shown in FIGS. 1 and 2, wherein FIG. 1 shows a longitudinal section of the arrangement, whereas FIG. 2 shows a transverse section thereof.

The arrangement has a container which includes a cylindrical wall 1 constituted by glass and two end walls 2. The end walls 2 are connected with one another by tightening bolts 4 and nuts 5. The cylindrical wall 1 together with the end walls 2 bound an inner chamber of the container. The end walls 2 are provided with openings 6 for introducing air or oxygen-containing gas into the inner chamber of the container or withdrawing the same from the inner chamber of the container. Further openings 7 serve for supplying a nutrient medium into the inner chamber of the container and for emptying the same after termination of the process of cultivation.

A plurality of tubular supporting elements 11 are located in the inner chamber of the container. The tubular supporting elements are rotatable about an axis of the container. A rotatable axle 8 defines the axis of rotation of the tubular supporting elements 11 and carries two end discs 9 which are mounted on the axle 8 and support end portions of the tubular supporting elements 11.

Each of the tubular supporting elements 11 bounds an inner passage and has an inner diameter which is equal from 8 to 25 mm., preferably 19–22 mm. Each end portion of each tubular supporting element 11 extends through a respective opening in a respective one of the end discs 9 and is fixed therein by means of an O-ring. In dependence upon the dimensions of the arrangement, one or more additional disc 10 may be provided for supporting the tubular supporting elements 11 in the regions located between the end discs 9.

Figure 6:
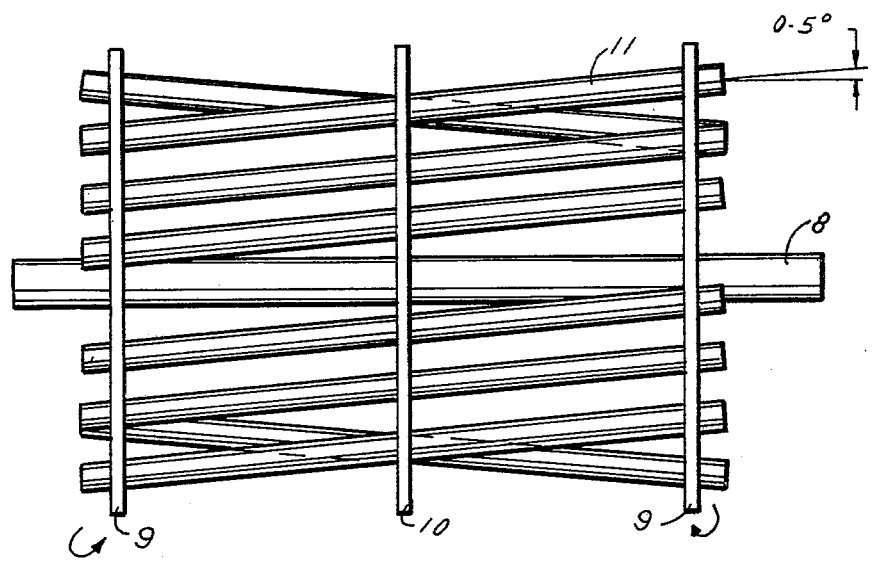
FIG. 6 is a view showing the tubular supporting elements in the position in which they are inclined relative to a horizontal axis.

Generally, the tubular supporting elements 11 extend in an axial direction which corresponds to their horizontal position. However, the whole pack of the tubular supporting elements 11 can be displaced so that the latter are offset from the horizontal position whereby each individual tubular element 11 becomes inclined relative to a horizontal. This can be performed by turning of the end discs 9 in two mutually opposite directions, as shown particularly in FIG. 6. The inclination of the individual tubular supporting elements 11 may be equal to maximum 5°.

An electric motor 12 imparts rotation to the axles 8 through a cone belt 13 and a disc 14. The axle 8, in turn, rotates the end discs 9 and the additional disc 10 so that the tubular supporting elements also rotate about the axis. The axle 8 is supported by the end walls 2 of the container in known manner.

Figure 3:
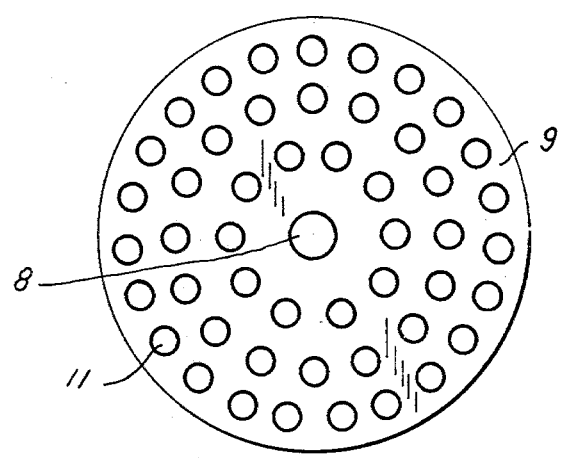
FIG. 3 is a view showing a disc which supports tubular supporting elements of the arrangement.

FIG. 3 shows the individual end disc 9 which can also be used as the additional disc 10 for supporting the tubular supporting elements 11 in the intermediate e.g. central regions. It has a plurality of the above-mentioned openings through which the end portions of the tubular supporting elements 11 extend.

Figure 4:
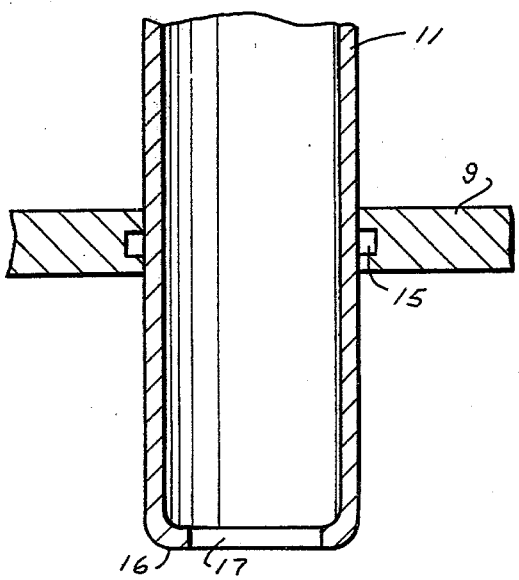
FIG. 4 is a view showing an end portion of the individual tubular supporting element.

FIG. 4 shows the end portion of one of the tubular supporting elements 11. The end portion of the supporting element 11 is fixed to the end disc 9 by means of the O-ring 15. The tubular supporting element 11 has an end section 16 which extends radially inwardly toward an axis of the respective tubular supporting element. This end section 16 bounds an end opening 17 which communicates with an inner passage of the tubular supporting element 11. The end section 16 extends at an angle which is selected with the due regard of the consistency of the nutrient medium.

Figure 5:
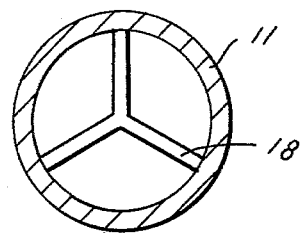
FIG. 5 is a view showing an additional supporting element which is located in an inner passage of the tubular supporting element.

As shown particularly in FIG. 5, an additional supporting element 18 is located in the inner passage of each of the tubular supporting elements 11. The additional supporting elements 18 serve for increasing the surfaces on which the cells can be cultivated. Each of the additional supporting elements 18 is formed by plates which are arranged in star-like manner. The additional supporting elements 18 are constituted by polycarbonate or another synthetic plastic material which preferably is heat-resistant.

In order to cultivate the cells, a nutrient medium is introduced into the container through the openings 7 and so that it covers the tubular supporting elements 11 which are located below the axle 8. Not all tubular supporting elements 11 located above the axle 8 have to be covered by the nutrient medium. The pack of the tubular supporting elements 11 is driven for rotation by the axle 8 through the discs 9 and 10, after admission into the container the cells to be grown. The axle 8 is driven by the electric motor 12 through the cone belt 13 and the disc 14.

The tubular supporting elements 11 can be inclined relative to their horizontal position by means of turning of the end discs 9 in two mutually opposite directions. As a result of this, the nutrient medium flows through the inner passages of the tubular supporting elements 11, whereas the latter rotate at a speed equal to from 5 to 20 revolutions per hour. The end sections 16 of the tubular supporting elements 11 extend radially inwardly toward the axes of the tubular supporting elements and thereby retard the flow of the nutrient medium through the inner passages of the latter. In such a construction a longer moistening of the cells in the inner passages of the tubular supporting elements 11 is guaranteed.

Instead of the end sections 16, silicone tubular members having the length from 1 to 2 cm may be inserted into the end portions of the tubular supporting elements 11. It has also been shown that on the outer surfaces of the tubular supporting elements 11 a lower but still satisfactory growth of the cells is attained.

Gases which are needed for the cultivation of the cells are supplied through one of the openings 6 and withdrawn through the other opening 6. A required sterilizing filter is known per se and for this reason is not shown in the drawing.

After termination of the process of growing, the cells are removed from supporting surfaces in known manner. A subsequent inoculation by viruses is possible without withdrawl of the cells from the container.

It will be understood that each of the elements described above, or two or more together, may also find a useful application in other types of constructions differing from the types described above.

While the invention has been illustrated and described as embodied in an arrangement for cultivating cells of animal and human tissues in a monocellular layer and the like, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An apparatus for cultivating cells of animal and human tissues, comprising a container which forms an inner chamber having an axis; means for introducing a nutrient medium into said inner chamber so as to at least partially fill the latter; a plurality of tubular cell supporting elements located in said chamber and extending substantially in an axial direction of the latter, each of said tubular cell supporting elements forming an inner passage and having an inner surface and an outer surface, the inner passage of each of said tubular cell supporting elements having an axis and two axially spaced open ends, so that the nutrient medium not only surrounds said tubular cell supporting elements from outside but also fills said inner passages, and cells are cultivated both on the inner surfaces and on the outer surfaces of said tubular cell supporting elements; means for rotating said tubular cell supporting elements about said axis of said inner chamber and including an axle defining said axis and connected with said tubular cell supporting elements for joint rotation therewith; and means for tilting said tubular cell supporting elements from the horizontal, so that one of said open ends of each of said inner passages is located above the other of said open ends, whereby the nutrient medium flows in each of said inner passages from said one end toward said other end, said tilting means including at least two discs arranged for connecting and supporting said tubular cell supporting elements wherein said tubular cell supporting elements are loosely fixed in said discs on said axle, said discs being turnable about said axis of said inner chamber of said container in two mutually opposite directions so as to tilt said tubular cell supporting elements from the horizontal.

2. An apparatus as defined in claim 1, wherein each of said tubular cell supporting elements has two axially spaced end portions and a central portion located therebetween, said discs supporting said end portions of said tubular cell supporting elements; and further comprising at least one additional disc supporting said central portion of said tubular cell supporting elements.

3. An apparatus as defined in claim 1; and further comprising means for loosely fixing said tubular cell supporting elements to said discs and including a plurality of O-rings each arranged for fixing one of said tubular cell supporting elements to one of said discs.

4. An apparatus as defined in claim 1, wherein said inner passage of each of said tubular cell supporting elements has a diameter between 8 and 25 mm.

5. An apparatus as defined in claim 1, further comprising additional supporting means for supporting the cells and positioned in the inner passage of each of said tubular cell supporting elements.

6. An apparatus as defined in claim 5, wherein said additional supporting means comprises a plurality of additional cell supporting elements connected to the inner surface of each of said first mentioned tubular cell supporting elements.

7. An apparatus as defined in claim 6, wherein said additional cell supporting elements extend radially inside of each of said first-mentioned tubular cell supporting elements.

8. An apparatus as defined in claim 6, wherein said additional cell supporting elements are polycarbonate.

9. An apparatus as defined in claim 1, wherein said tubular cell supporting elements are glass.

10. An apparatus as defined in claim 1, wherein said tubular cell supporting elements are tiltable from the horizontal by an angle which is at most equal to 5°.

11. An apparatus as defined in claim 1, wherein each of said inner passages of said tubular cell supporting elements has a predetermined diameter; and further comprising means for retarding the flow of the nutrient medium through said inner passages of said tubular cell supporting elements, said retarding means including a wall section extending radially inwardly from a wall of each of said tubular cell supporting elements in the region of each of said open ends so as to reduce the diameter of each of said passages in said regions.

* * * * *